ABSTRACT ve of the metal being sampled and closer in correlation

United States Patent [19]

Falk

[11] 4,051,732
[45] Oct. 4, 1977

[54] MOLTEN METAL STREAM SAMPLER

[76] Inventor: Richard A. Falk, 519 Westminster Drive, Waukesha, Wis. 53186

[21] Appl. No.: 683,440

[22] Filed: May 4, 1976

[51] Int. Cl.$^2$ ............................................. G01N 1/12
[52] U.S. Cl. ............................ 73/425.4 R; 73/DIG. 9
[58] Field of Search ...................... 73/DIG. 9, 425.4 R

[56] References Cited

U.S. PATENT DOCUMENTS

| 3,859,857 | 1/1975 | Falk | 73/DIG. 9 |
| 3,897,689 | 8/1975 | Boron | 73/DIG. 9 |
| 3,913,404 | 10/1975 | Boron | 73/DIG. 9 |

Primary Examiner—S. Clement Swisher

Attorney, Agent, or Firm—Henry C. Fuller

[57] ABSTRACT

A stream sampler includes split metal mold halves for forming a disc sample and a pin sample tube which extends through the walls of the disc mold into the interior of the disc to provide a pin sample which has little or no decarburization and thus, more representative of the metal being sampled and closer in correlation in carbon percent to the disc sample. The pin sample tube is enclosed by a heat resistant insulative glass sleeve which extends beyond the end of the pin sample tube. The extension enhances filling of the pin sample tube by capillary action and provides a reservoir of metal to isolate the remote end of the pin sample from air and minimize decarburization.

7 Claims, 3 Drawing Figures

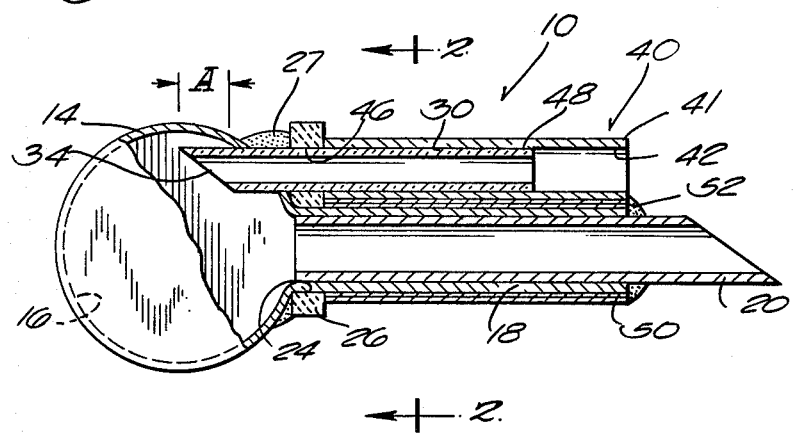
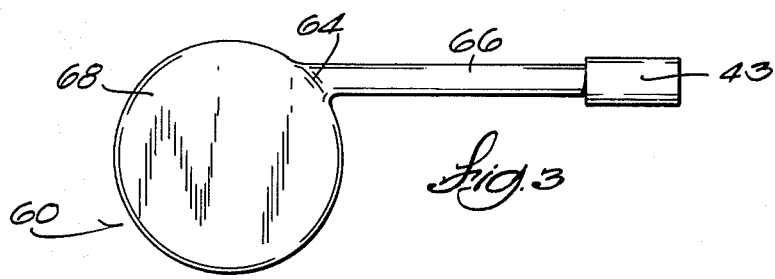
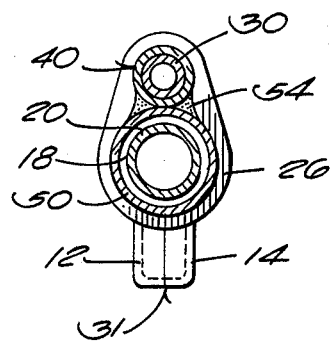

MOLTEN METAL STREAM SAMPLER

BACKGROUND OF INVENTION

Although stream samplers with pin sample tubes have been known and used for some time as illustrated in my U.S. Pat. No. 3,859,857, the pin sample carbon analysis does not correlate very closely with the disc analysis. Typically, there are very large differences in carbon between the pins and the disc samples with errors in the range of 0.22 to 1.00% carbon. In addition, to my knowledge pin samples regardless of how they are taken, have a random variation in carbon throughout the sample length and a reduction in the percentage of carbon in the first 60% of the length of the pin sample from the pin sample tube inlet in the disc mold. The purpose of the invention disclosed herein is to provide a more representative pin sample with close correlation in chemistry with the disc sample.

SUMMARY OF INVENTION

It has been concluded from test results that it is desirable to locate the pin sample tube inlet a distance away from the metal disc mold to prevent exposure of the molten metal entering the pin sample tube to air present in the gap between the disc mold walls and thus, minimize decarburization of the steel entering the pin sample tube. Accordingly, the pin sample tube entrance of the sampler disclosed herein is located away from the wall. The inner end of the pin sample tube can be beveled and faces toward the center of the disc mold.

Use of the beveled tip also increases the cross-sectional area of the inlet into the pin tube which increases the flow rate into the tube. In addition, the added mass of hot metal at the end of the beveled tip enlarges the cross-sectional area of the inlet through which heat from the molten metal in the disc communicates with the metal in the pin sample tube to stabilize the temperature of the metal at the inlet and reduce the temperature gradient along the pin for more uniform cooling of the pin.

Other features of the invention include a heat resistant glass or Pyrex sleeve which surrounds the pin sample tube and provides an insulating effect to reduce the cooling rate. The shroud also functions to support the tube and eliminates the need for refractory cement along the pin sample tube in direct contact with the pin sample tube. Minimizing the cement contact at various points along the pin sample tube as is found in prior art samplers, reduces or decreases spot cooling of the pin which is believed to cause localized carbon variations in the pin.

The sleeve extends beyond the end of the pin sample tube and forms a reservoir for the initial metal flowing through the pin sample tube to provide a plug which seals the remote end of the pin sample tube from air which otherwise would decarburize the end of the pin sample.

Further objects, advantages and features of the invention will become apparent from the following disclosure.

DESCRIPTION OF DRAWINGS

FIG. 1 is a side view in fragmentary section of a stream sampler embodying the present invention.

FIG. 2 is a sectional view along line 2—2 of FIG. 1.

FIG. 3 is a side view of a sample taken with the mold shown in FIG. 1.

DESCRIPTION OF PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

In the drawings, FIG. 1 shows a stream sampler 10 which includes split mold halves 12 and 14 which define a cavity 16 for obtaining a disc sample. The split mold halves include projecting portions 18 in the form of half tubular cylinders which support an inlet or fill tube 20 which is inserted in the stream of metal to obtain the sample. The projecting portions 18 extend through an aperture 24 in a refractory disc 26. The projecting portions 18 can be cemented to the disc by refractory cement 27.

The pin sample tube 30 can have a beveled end 32 which faces toward the center of the cavity 16. The pin sample tube 30 desirably extends into the tube so that dimension A is at least a quarter inch. This locates the inlet 34 of the pin sample tube a distance away from the inner wall surfaces of the mold halves 12, 14 which avoids exposure of the metal entering the pin sample tube to air present at the gap 31 between the mold halves 12, 14. Such air exposure can cause decarburization of the steel entering the pin tube 30. With the pin sample tube projecting into the mold cavity as disclosed, the pin sample tube is filled with metal from the interior of the mold which is not exposed to outside air.

The pin sample tube 30 is insulated by a Pyrex or refractory tube or shroud 40 which receives the pin sample tube 30 in the interior 42. The pin sample tube 30 also extends through an aperture 46 in the refractory disc 26. Use of the shroud 40 reduces the cooling rate of the sample in the tube 30 and results in more uniform cooling and thus, more representative chemistry. It has been found that extending the insulative tube 40 beyond the end 48 of the pin sample tube 30, provides better samples. The extending sleeve portion 41 provides a reservoir for the metal flowing through the pin sample tube 30 and forms a plug 43 (FIG. 3) at the end 48 of the pin sample tube 30 which seals the end 48 of the tube 30 to isolate the pin sample from the air and minimize decarburization caused by air exposure. The extending sleeve portion 41 also provides additional tube length to provide increased capillary action for effective filling of the pin sample tube.

A paperboard sleeve 50 can be employed to protect the fill tube 20 and provide support for the tube 40 which can be cemented at 52 and 54 with refractory cement to the paperboard sleeve and refractory disc 26. Use of the shroud 40 also prevents spot cooling of the pin caused in prior art devices by refractory cement contact points with the pin sample tube.

FIG. 3 shows a sample 60 cast with the mold shown in FIG. 1. As a result of the bevel 34 on the pin sample tube 30, the cross section of the sample 60 at the juncture 64 of the pin sample portion 66 and disc 68 is larger than the cross section of metal which occurs, if the pin sample tube has an inlet plane at right angles with the tube axis. Thus, the metal connection between the pin 66 and disc 68 is larger and results in more heat energy being conducted from the disc 68 to the pin 66 which minimizes the temperature gradient through the pin for more uniform cooling and thus, provides more uniform carbon chemistry in the pin 66.

A test with the sampler disclosed herein provided an average carbon value in the disc 68 of 0.74% and an average in the pin 66 of 0.736% carbon thus, demonstrating the close correlation between the pin and disc. The standard deviation of carbon in the disc was 0.0122% and the deviation in the pin 0.016%.

I claim:

1. A molten metal sampler comprising wall means defining a mold cavity for forming a sample, wall means defining a sample entry passage having an inlet for receiving molten metal and an outlet communicating with said mold cavity, an aperture in said wall means, a pin sample tube extending through said aperture and having an inner end located in said mold cavity remote from the wall means to obtain metal from the interior of said mold cavity to minimize decarburization of the pin sample.

2. A molten metal sampler in accordance with claim 1 wherein said stream sampler tube projects through said wall means at least one quarter of an inch.

3. A molten metal sampler in accordance with claim 1 including a heat resistant refractory shroud having a through aperture and wherein said pin sample tube extends through a substantial portion of the length of said shroud.

4. A stream sampler in accordance with claim 3 wherein said shroud comprises a heat resistant glass tube.

5. A molten metal sampler in accordance with claim 3 wherein said shroud extends beyond said pin sample tube to form a metal reservoir to mold a plug which seals the end of the pin sample tube from air exteriorly of the pin sample tube.

6. A sampler in accordance with claim 1 wherein the inner end of said pin sample tube is beveled and faces the interior of the mold cavity.

7. A sampler in accordance with claim 1 wherein said inner end of said fill tube is beveled and faces the center of the mold cavity.

* * * * *